(12) United States Patent
Theodorson (10) Patent No.: US 11,330,674 B2
(45) Date of Patent: May 10, 2022

(54) RADIANT HEAT FOOT WARMING DEVICE(S)

(71) Applicant: Robert P. Theodorson, Arlington, VA (US)

(72) Inventor: Robert P. Theodorson, Arlington, VA (US)

(73) Assignee: Robert P. Theodorson, Arlington, VA (US)

( * ) Notice: Subject to any disclaimer, the term of this patent is extended or adjusted under 35 U.S.C. 154(b) by 299 days.

(21) Appl. No.: 16/675,638

(22) Filed: Nov. 6, 2019

(65) Prior Publication Data

US 2020/0154525 A1 May 14, 2020

Related U.S. Application Data

(60) Provisional application No. 62/757,374, filed on Nov. 8, 2018.

(51) Int. Cl.
| | |
|---|---|
| *A61F 7/08* | (2006.01) |
| *H05B 3/24* | (2006.01) |
| *H05B 3/04* | (2006.01) |
| *A61F 7/00* | (2006.01) |

(52) U.S. Cl.
CPC .............. *H05B 3/24* (2013.01); *A61F 7/08* (2013.01); *H05B 3/04* (2013.01); *A61F 2007/0045* (2013.01)

(58) Field of Classification Search
CPC combination set(s) only.
See application file for complete search history.

(56) References Cited

U.S. PATENT DOCUMENTS

| | | | | |
|---|---|---|---|---|
| 2014/0209594 | A1* | 7/2014 | Besner | A61F 7/007 219/217 |
| 2015/0182406 | A1* | 7/2015 | Falk | A61F 7/10 600/22 |
| 2017/0266039 | A1 | 9/2017 | Song | |
| 2017/0290700 | A1 | 10/2017 | Guillaume | |

FOREIGN PATENT DOCUMENTS

| | | | | |
|---|---|---|---|---|
| GB | 2290475 A | * | 1/1996 | ........... A61H 1/0237 |
| GB | 2290475 A | | 1/1996 | |
| KR | 20060018431 A | | 3/2006 | |
| KR | 20080005291 U | | 11/2008 | |
| KR | 20080005710 U | | 11/2008 | |
| WO | 2006024938 A2 | | 3/2006 | |

OTHER PUBLICATIONS

Extended European Search Report dated Feb. 6, 2020 for EP Patent Application No. EP 19208173 (7 pages).

* cited by examiner

*Primary Examiner* — Tigist S Demie (74) *Attorney, Agent, or Firm* — Shumaker, Loop & Kendrick, LLP (57) ABSTRACT

A radiant heat foot warming device including a top planar surface configured to emanate radiant heat therefrom to warm feet of a user; a bottom planar surface spaced apart from the top planar surface; a plurality of curved sidewalls positioned between and connected to the top planar surface and the bottom planar surface; and an adjustable temperature control member positioned on the top planar surface that displays device temperature and further adjustably controls device temperature to regulate radiant heat emanating from the top planar surface.

7 Claims, 10 Drawing Sheets

FIG. 12C

US 11,330,674 B2

RADIANT HEAT FOOT WARMING DEVICE(S)

TECHNICAL FIELD

The present invention relates generally to the field of foot warming devices, and more particularly, to radiant heat foot warming devices for use during outdoor events (e.g., sporting events).

BACKGROUND

Often during sporting events, an athlete is likely to encounter a variety of adverse conditions that may inhibit the athlete's performance. Numerous devices and formulations have been provided in the past to counteract these conditions and to optimize the athlete's performance. For example, sports drinks have been formulated to replace an athlete's depleted endogenous electrolytes thereby reducing and/or preventing cramping during the athletic event. In hot, humid sub-tropical environments, cooling-misting fans are often provided so that an athlete can remain cool and/or cool down rather quickly thereby improving the athlete's overall comfort level and performance during the sporting event. Likewise, space heaters are sometimes used to heat a large area but heat readily dissipates due to range limitation, indirect focus of the heat, etc.

While many devices and formulations exist that are intended to improve an athlete's performance such as those discussed above, little exists directed to maintaining optimal foot conditions for the athlete. For example, in extremely cold weather climates, the athlete is relegated to place "hand warmers" within their socks to provide warmth thereto, and in moist, damp environments (and/or inclement weather conditions such as raining), little and/or no relief is currently provided to the athlete to alleviate these conditions. Frostbite has been and continues to be a serious concern for outdoor athletes who rely on their feet being a nominal temperature in order to play, namely European football (soccer) and American football athletes.

SUMMARY

Therefore, a need exists to provide a device that mitigates the above mentioned environmental conditions, which further creates optimal conditions for an athlete's feet regardless of environmental conditions (e.g., extremely cold and/or moist/wet environment). Thus, disclosed are radiant heat foot warming devices that mitigate the deleterious effects on an athlete's performance often associated with extremely cold and/or moist/wet environments during a sporting event. In certain aspects disclosed is a radiant heat foot warming device including: (a) a top planar surface configured to emanate radiant heat therefrom to warm feet of a user; (b) a bottom planar surface spaced apart from the top planar surface, the bottom planar surface is configured to directly contact a ground surface and to not emanate heat therefrom; (c) a plurality of curved sidewalls positioned between and connected to the top planar surface and the bottom planar surface, the plurality of sidewalls do not emanate heat therefrom; and (d) an adjustable temperature control member positioned on the top planar surface that displays device temperature and further adjustably controls device temperature to regulate radiant heat emanating from the top planar surface.

In certain aspects, the device further includes a charging port positioned on one sidewall of the plurality of sidewalls.

In certain aspects, the device further includes a rechargeable power source, a circuit, and a plurality of heating elements that are each housed within the device with the rechargeable power operably connected to a charging port and circuit, and the circuit is operably connected to the adjustable temperature control member.

In certain aspects, the plurality of heating elements are positioned directly adjacent to a bottom surface of the top planar surface within the device and are selectively grouped together to form heating zones emanating from the outermost surface of the top planar surface that are recessed from peripheral edges of the device.

In certain aspects, the plurality of heating elements are operably connected to the adjustable temperature control member.

In certain aspects, the plurality of heating elements are grouped together to form two spaced apart heating zones that are parallel to one another with each zone being adjustable to independently control the temperature in each zone.

In certain aspects, each heating zone is further configured to conform to contours of the user's feet and is further configured to concurrently massage and heat the user's feet.

In certain aspects each heating zone is further configured to continuously or intermittently massage and to continuously or intermittently heat the user's feet. In certain aspects, the device is configured for only a single user. In certain aspects, the device is configured for a plurality of users.

In certain aspects, also disclosed is a radiant heat foot warming assembly including: (a) a waterproof outer sheath configured to maintain dryness and/or prevent water intrusion internally within the waterproof outer sheath and to maintain a dry environment in which a radiant foot warming device is positioned; and (b) a radiant foot warming device that is completely positioned internally within the waterproof outer sheath, the radiant heat foot warming device including: (i) a top planar surface configured to emanate radiant heat from one or more heating zones to warm feet of a user; (ii) a bottom planar surface spaced apart from the top planar surface, the bottom planar surface is configured to not emanate heat therefrom; (iii) a plurality of curved sidewalls positioned between and connected to the top planar surface and the bottom planar surface, the plurality of sidewalls do not emanate heat therefrom; and (iv) an adjustable temperature control member positioned on the top planar surface that displays device temperature and further adjustably controls device temperature to regulate radiant heat emanating from the top planar surface.

In certain aspects, the waterproof outer sheath includes a thermally conductive material configured to maintain heat emanating from the radiant heat foot warming device internally within the assembly to reduce, minimize, and/or eliminate heat dissipation externally outside of the assembly.

In certain aspects, the waterproof outer sheath includes a first opening aligned with the one or more heating zones on the top planar surface of the radiant foot warming device and arranged to form an internal compartment positioned internally within the assembly between the outer sheath and top planar surface of the radiant foot warming device that is configured to receive and heat a user's feet therein while maintaining a dry environment and/or preventing water intrusion within the internal compartment.

In certain aspects, a resiliently deformable elastomeric seal is further included and is affixed to peripheral edges of the first opening of the outer sheath and extending inwardly from the peripheral edges of the first opening of the outer sheath towards a center of the first opening, the resiliently deformable elastomeric seal having a slit arranged in the center of the first opening that is configured to temporarily open while receiving the user's feet therethrough and to resiliently close around the user's ankle and/or leg when the user's feet are positioned within the internal compartment to maintain a dry environment and/or preventing water intrusion within the internal compartment.

In certain aspects, the outer sheath includes a second opening aligned with the adjustable temperature control such that that the device temperature and temperature controls are viewable and accessible by the user. It should be further noted that the sheath may have additional openings formed therein that are configured to align with, for example, charging ports and/or USB ports on the radiant heat foot device.

In certain aspects, the outer sheath is a waterproof nylon material.

In certain aspects, the waterproof nylon material is rip stop nylon.

In certain aspects, the radiant heat foot warming device is removable from and re-insertable within the waterproof outer sheath.

In certain aspects, the radiant heat foot warming device is permanently positioned within the outer sheath.

Embodiments of the invention can include one or more or any combination of the above features and configurations.

Additional features, aspects and advantages of the invention will be set forth in the detailed description which follows, and in part will be readily apparent to those skilled in the art from that description or recognized by practicing the invention as described herein. It is to be understood that both the foregoing general description and the following detailed description present various embodiments of the invention, and are intended to provide an overview or framework for understanding the nature and character of the invention as it is claimed. The accompanying drawings are included to provide a further understanding of the invention, and are incorporated in and constitute a part of this specification.

BRIEF DESCRIPTION OF THE DRAWINGS

These and other features, aspects and advantages of the present invention are better understood when the following detailed description of the invention is read with reference to the accompanying drawings, in which.

DETAILED DESCRIPTION

The present invention will now be described more fully hereinafter with reference to the accompanying drawings in which exemplary embodiments of the invention are shown. However, the invention may be embodied in many different forms and should not be construed as limited to the representative embodiments set forth herein. The exemplary embodiments are provided so that this disclosure will be both thorough and complete, and will fully convey the scope of the invention and enable one of ordinary skill in the art to make, use and practice the invention. Like reference numbers refer to like elements throughout the various drawings.

FIGS. 1-9 depict a first embodiment of the contemplated radiant heat foot warming device 100. Specifically disclosed are radiant heat foot warming devices 100 that mitigate the deleterious effects on an athlete's performance often associated with extremely cold and/or moist/wet environments during a sporting event. These devices preferably warm and/or dry the user's feet during the event thereby maintaining optimal conditions for the user's feet regardless of the weather conditions.

In particular and as shown in FIGS. 1-5, the radiant heat foot warming device 100 includes (a) a top planar surface 101 configured to emanate radiant heat (RH) therefrom to warm feet of a user; (b) a bottom planar surface 103 spaced apart from the top planar surface with the bottom planar surface being configured to directly contact a ground surface as to separate the user's feet from a cool/cold/wet surface effected by weather elements; (c) a plurality of curved sidewalls 105, 106, 107, 108 positioned between and connected to the top planar surface and the bottom planar surface; and (d) an adjustable temperature control member 111 positioned on the top planar surface 101 that displays device temperature and further adjustably controls device temperature to regulate radiant heat emanating from the top planar surface as desired by the user.

In certain aspects, each of the top planar surface 101, bottom planar surface 103, and the plurality of sidewalls 105, 106, 107, 108 are formed of rigid non-deformable materials (e.g., durable rip stop nylon, water proof military grade made to US military specifications, rigid thermoplastic resin(s) such as polyethylene, cross-linked polyethylene, polypropylene, polyvinyl chloride, etc., metal, or a combination thereof), and the device is substantially waterproof to withstand and operate in harsh, inclement environments (e.g., cold weather and/or moist and/or rainy environments). In certain aspects, the bottom planar surface 103 and plurality of sidewalls 105, 106, 107, 108 do not emanate heat therefrom, and the bottom planar surface includes a high friction surface that grips the surface on which the surface is placed and further prevents and/or reduces inadvertent movement of the device.

As shown, for example in FIGS. 1, 2, 3, and 9, the radiant heat foot warming device 100 further includes a charging port 109 positioned on a sidewall (e.g., sidewall 105) that is configured with, for example, a USB port and/or USB connectivity. The radiant heat foot warming device further includes numerous internally positioned components such as a rechargeable power source, a circuit, and a plurality of heating elements that are operably connected to one another and are each completely housed within the device 100.

In certain aspects, the rechargeable power source (e.g., a rechargeable battery) is operably connected to the charging port 109 such that the rechargeable power source may be re-charged as desired and a circuit positioned internally within the device 100. The circuit is further operably connected to the adjustable temperature control member 111. As further alluded to above, the plurality of heating elements are positioned directly adjacent to a bottom surface (i.e., the surface internally located within the device) of the top planar surface 101 within the device and are selectively grouped together to form heating zones 120, 121 on the outermost surface of the top planar surface 101. The plurality of heating elements are further operably connected to the adjustable temperature control member 111 to selectively control heat emanating from the device.

Figure 1:
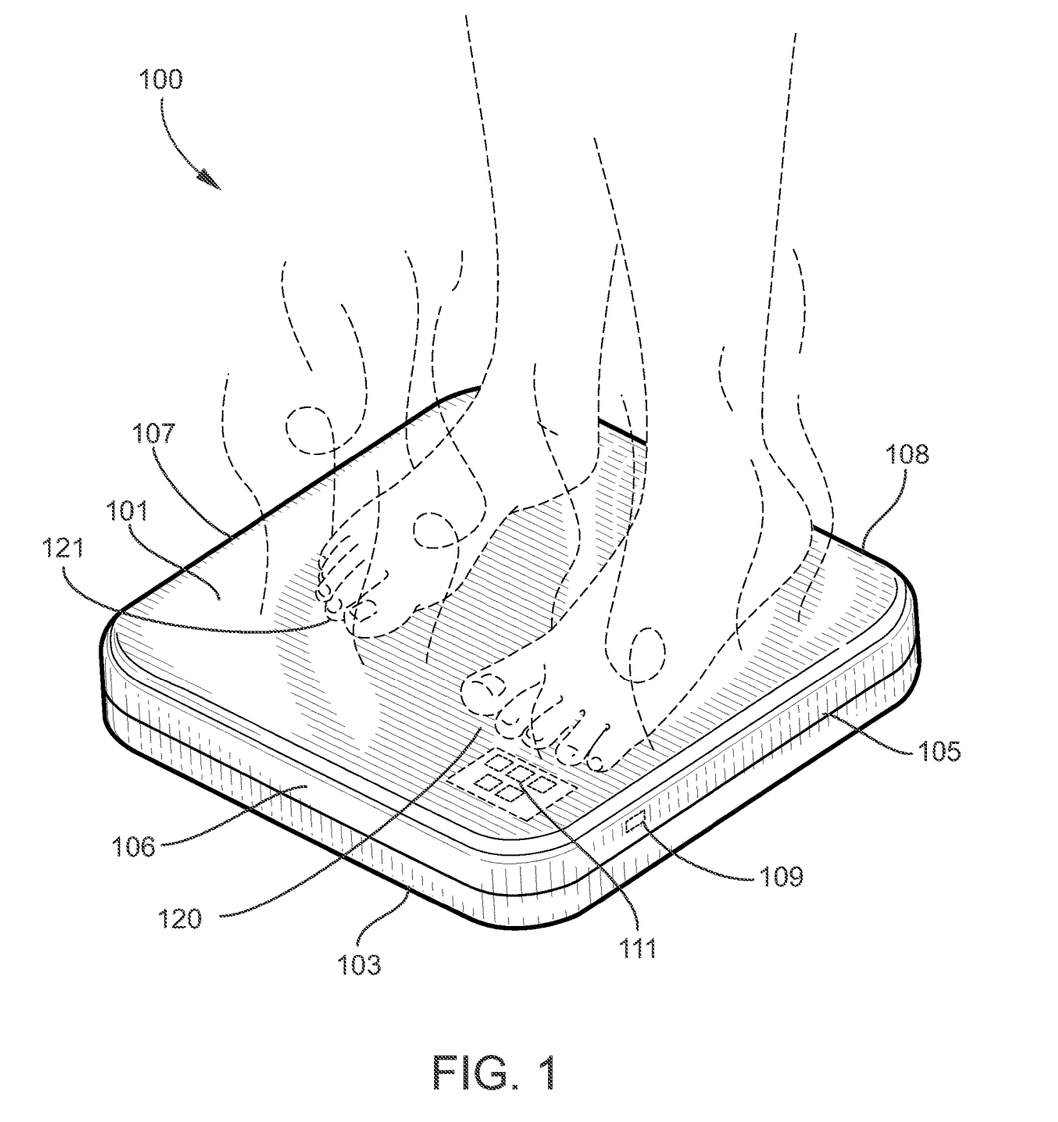
FIG. 1 is an environmental view of a radiant heat foot warming device shown with a user's feet placed thereon and radiant heat emanating therefrom according to a first embodiment.
Figure 2:
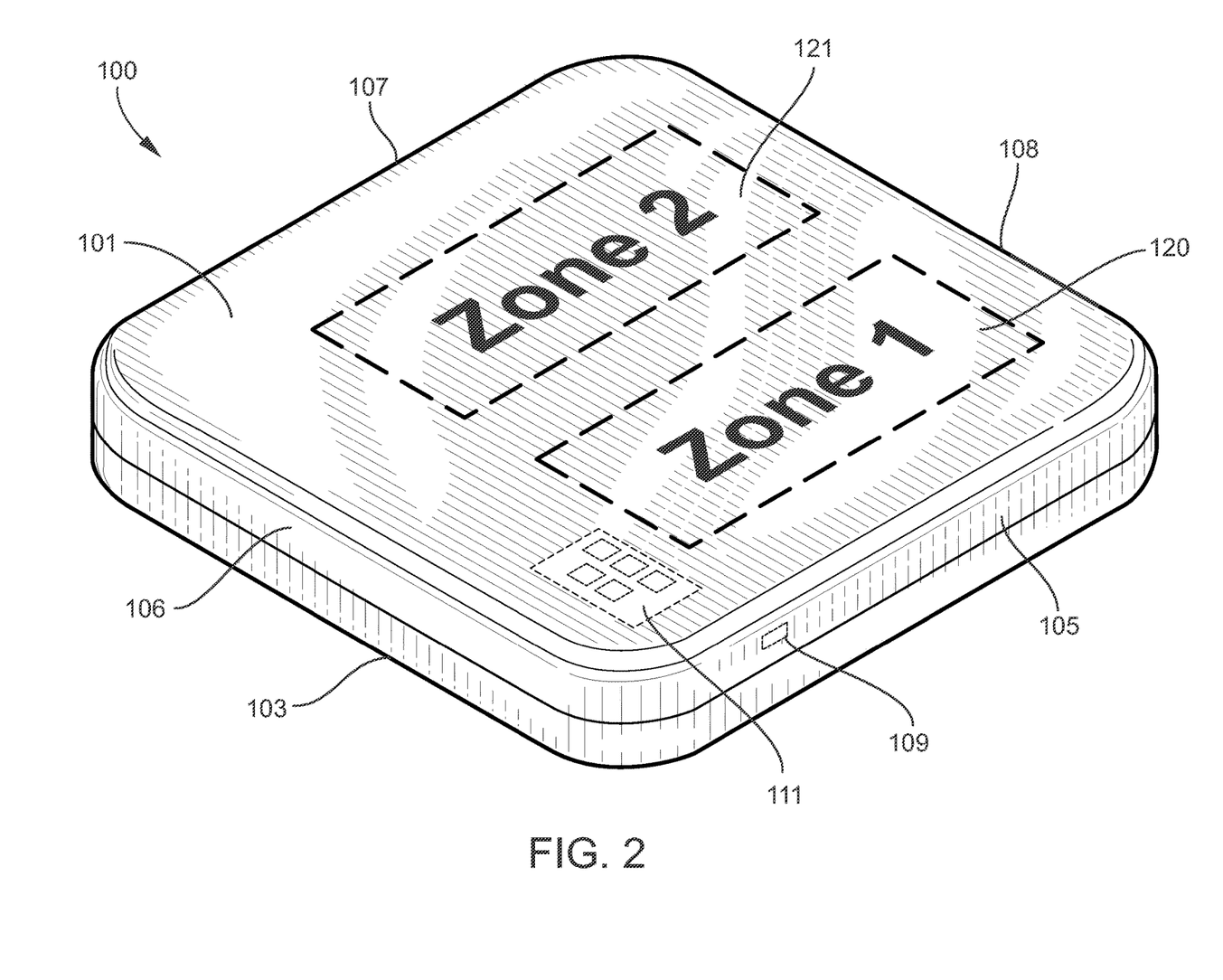
FIG. 2 a top perspective view thereof.
Figure 3:
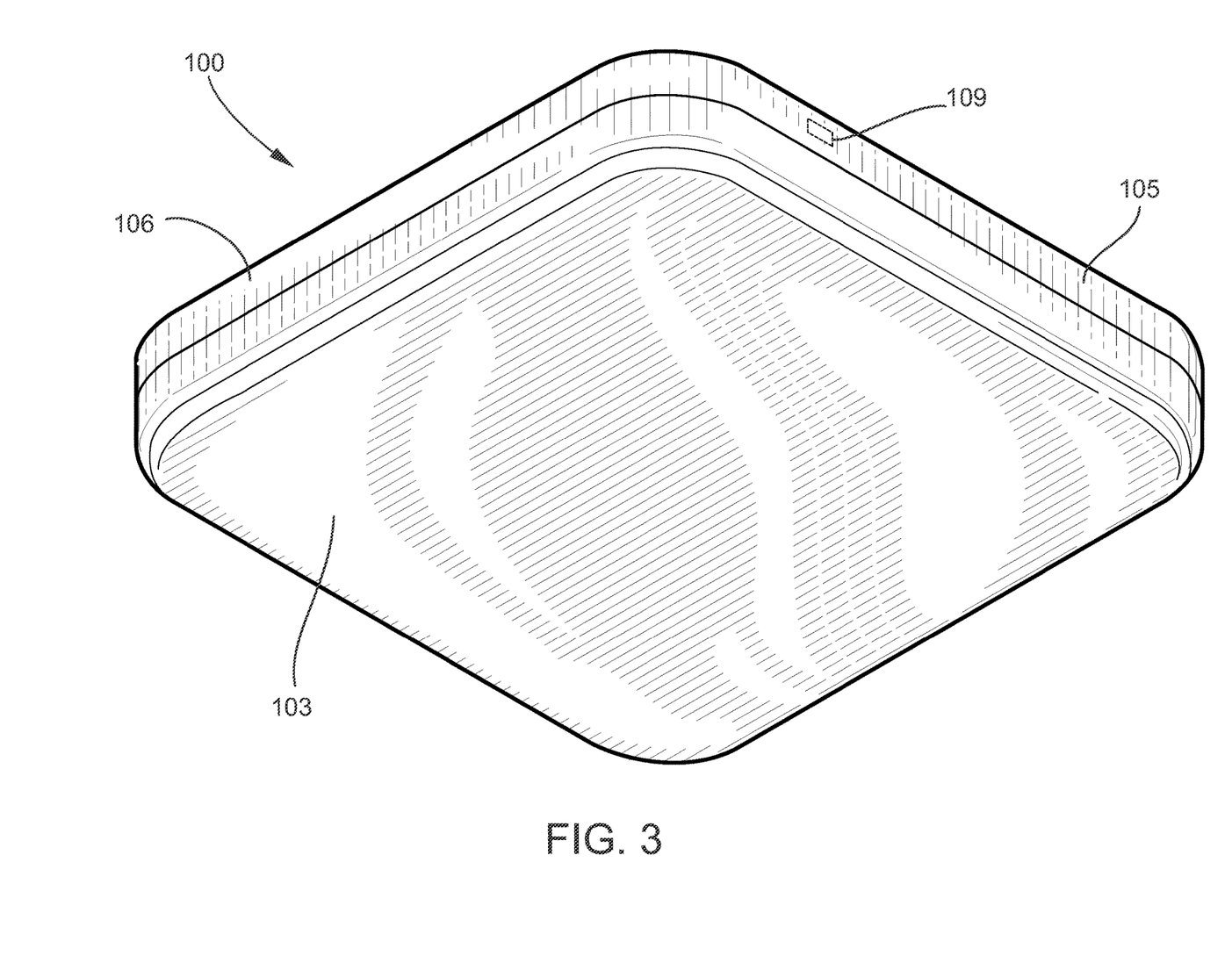
FIG. 3 is a bottom perspective view thereof.
Figure 4:
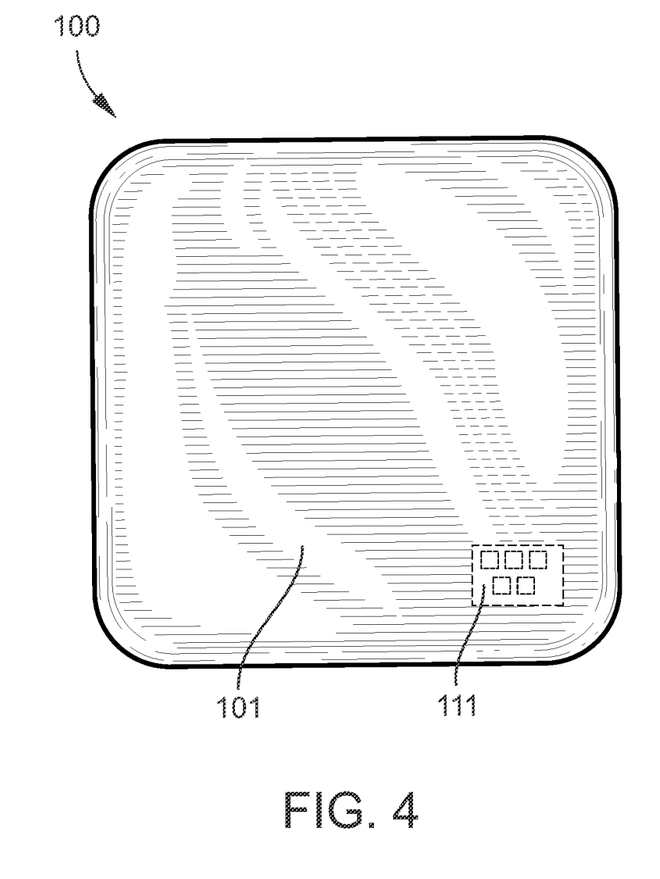
FIG. 4 is a top view thereof.
Figure 5:
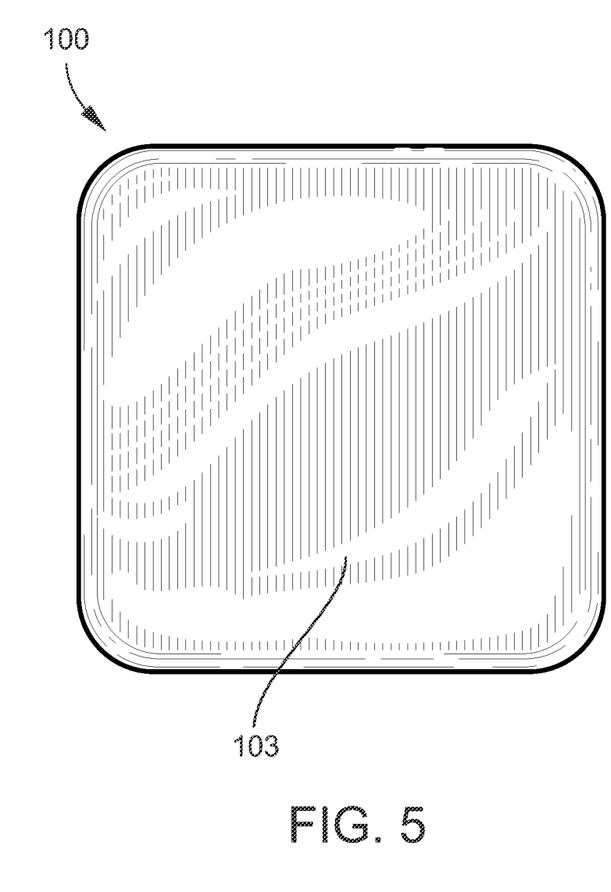
FIG. 5 is a bottom view thereof.
Figure 6:
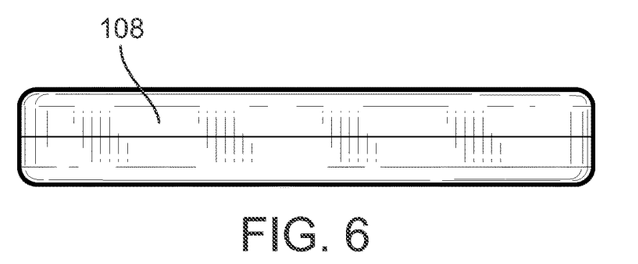
FIG. 6 is a front view thereof.
Figure 7:
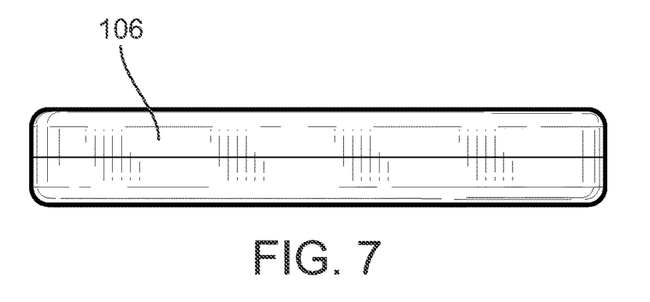
FIG. 7 is a back view thereof.
Figure 8:
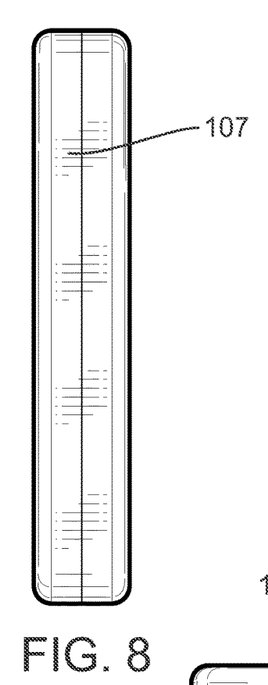
FIG. 8 is a right side view.
Figure 9:
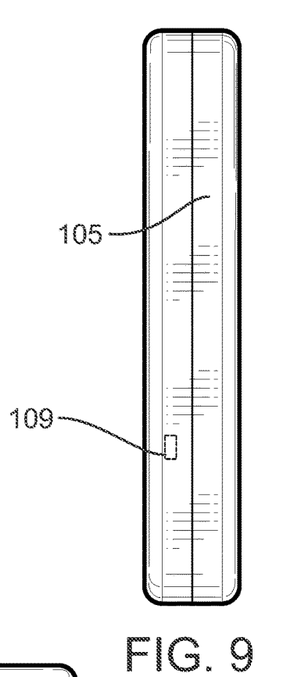
FIG. 9 is left side view thereof.

As further shown, for example, in FIG. 2, the heating zones 120, 121 are recessed and/or offset from peripheral edges of the device to reduce and/or prevent the user from slipping on the edges of the device when either placing the user's feet within the heating zones 120, 121 and/or removing the feet from the heating zones 120, 121 to resume the previous activity. In certain aspects, the heating zones may have different shapes and/or geometric conformations. For example, as shown in FIG. 2, the heating zones 120, 121 may be spaced apart and parallel to one another such that one foot of the user may be positioned on/in only one heating zone with each zone being independently adjustable to independently control the temperature in each zone.

In certain aspects, each zone 120, 121 may be formed from the same rigid material as the top planar surface 101. Alternatively, each zone 120, 121 may be formed of an elastically deformable material (e.g., a natural, synthetic rubber material, and/or a woven and/or non-woven fabric comprising preferably nylon fibers) that is configured to temporarily conform to the contours of the user's feet to either partially surround and encompass or completely surround and encompass the user's foot while placed in the heating zone but resiliently returns to its original state when the user has removed their foot/feet therefrom. Each heating zone 120, 121 may be substantially co-planar with the outermost surface of the top planar surface 101 or may alternatively be slightly recessed within the device 100 relative to the outermost surface of the top planar surface 101 thereby forming shallow pockets that receive a user's foot therein.

In certain aspects, each zone 120, 121 may be configured to provide additional functions. For example, each zone may be further configured to concurrently massage and/or vibrate the user's foot while emanating heat therefrom. In certain aspects, each zone 120, 121 is further configured to continuously or intermittently massage and to continuously or intermittently heat the user's feet. In this aspect, the temperature control member 111 may be further configured to control each of these additional functions such that each additional function may be independently used within each zone 120, 121 relative to the other zone.

FIGS. 1-9 depict the device 100 having a single user conformation. However, and as further shown in FIG. 10, multi-user devices 200 are further contemplated as a second embodiment.

Figure 10:
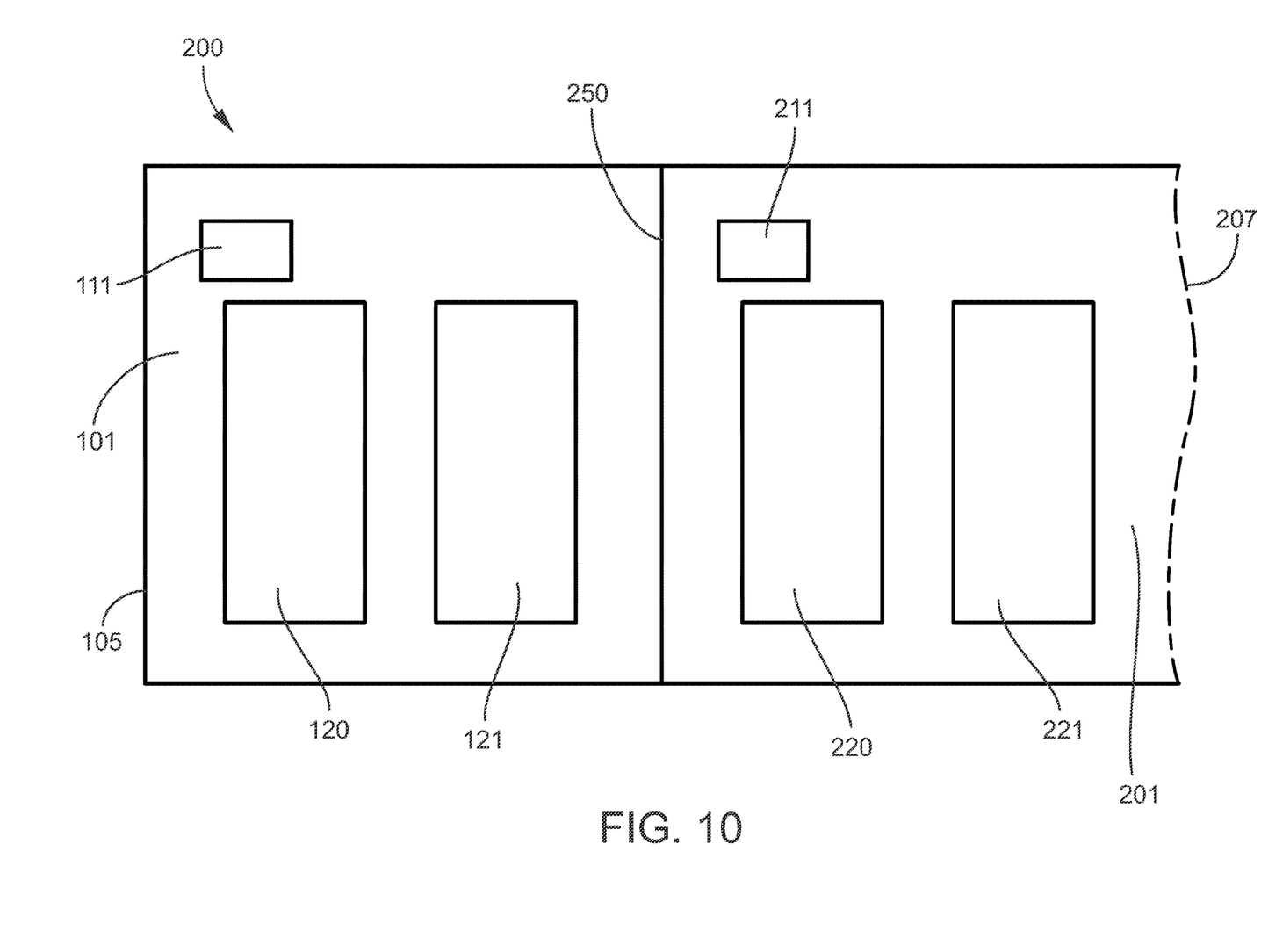
FIG. 10 depicts a second embodiment of the device that allows for multiple users to sit side by side in parallel and to further selectively warm each user's feet accordingly.

FIG. 10 specifically depicts a two user radiant heat foot warming device 200 where two users may be seated side by side with parallel heating zones to achieve parallel foot positioning of each user while in use. As specifically shown in FIG. 10, the multi-user device 200 is substantially similar to the device 100 of the first embodiment. However, instead of including sidewall 107, the second embodiment further includes a second top planar surface 201 connected the first top planar surface 101. Likewise, the second embodiment 200 further includes a second adjustable control member 111 operably connected to the second heating zones 220, 221 in the same manner as discussed above regarding the first embodiment. As further shown in FIG. 10, a partition 250 may be included on the multi-user device. Partition 250 may merely include indicia (e.g., a marking) placed on and between top planar surfaces 101, 201 indicating peripheral boundaries where each user's feet should be maintained to ensure a pleasurable experience by each user while the device 200 is in use. However, in certain additional aspects, partition 250 may be a physical partition attached to and extending away from the device 200 thereby physically separating the first top planar surface 101 from the second top planar surface. Broken line 207 further indicates either sidewall 207 and/or additional planar surfaces, heating zones, and adjustable control members connected in series to service the desired number of users. In certain aspects, the devices disclosed herein may include up to 6, 8, 10, 12, 14, 16, 18, or 20 heating zones and can further accommodate up to 3, 4, 5, 6, 7, 8, 9, or 10 users.

Figure 11:
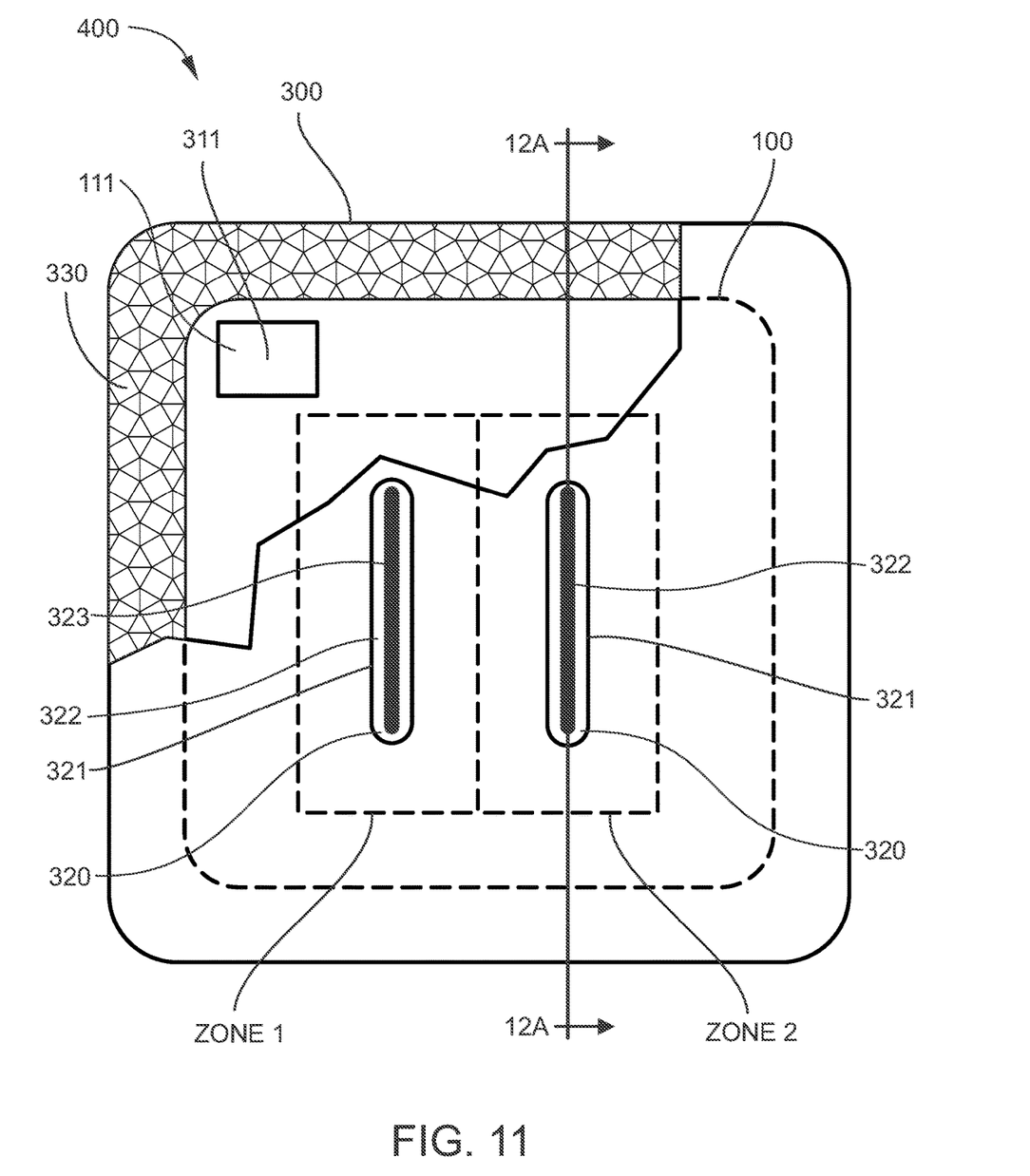
FIG. 11 depicts a radiant heat foot warming assembly having the radiant foot warming device positioned internally within a waterproof outer sheath, the waterproof outer sheath being configured to receive and heat a user's foot internally within the assembly while maintaining dryness and/or preventing water intrusion internally within the waterproof outer sheath.

FIG. 11 is an exemplary depiction of the radiant heat foot warming assembly 400 having the radiant foot warming device 100 positioned internally within the waterproof outer sheath 300, the waterproof outer sheath 300 being configured to maintain dryness and/or prevent water intrusion internally within the waterproof outer sheath 300 preferably at all times and especially during use of the radiant heat foot warming assembly. As specifically shown in FIG. 11, the radiant heat foot warming assembly 400 includes: (a) a waterproof outer sheath 300 configured to maintain dryness and/or prevent water intrusion internally within the waterproof outer sheath and to maintain a dry environment for the radiant foot warming device; and (b) a radiant foot warming device 100 that is completely positioned internally within the waterproof outer sheath 300, the radiant heat foot warming device includes: (i) a top planar surface 101 configured to emanate radiant heat from one or more heating zones 120, 121 to warm feet of a user; (ii) a bottom planar surface 103 spaced apart from the top planar surface, the bottom planar surface is configured to not emanate heat therefrom; (iii) a plurality of curved sidewalls 105, 106, 107, 108 positioned between and connected to the top planar surface and the bottom planar surface, the plurality of sidewalls do not emanate heat therefrom; and (iv) an adjustable temperature control member 111 positioned on the top planar surface that displays device temperature and further adjustably controls device temperature to regulate radiant heat emanating from the top planar surface.

Numeral 12A in FIG. 11 depicts the cross-section of views shown in exemplary assemblies 400 in FIG. 12A-12C, which will be discussed in further detail below. In view of the assemblies 400 shown in FIGS. 11-12C, the waterproof outer sheath 300 is comprised of a woven or non-woven material, which in certain aspects is deformable at least within the portions aligned with the device's heating zones that are configured to receive the user's feet in order to easily and comfortably accommodate feet of different sizes, and in certain instances and as further shown in FIGS. 11, 12A, and 12C, the assemblies may further include a thermally conductive padding or foam layer 330 (e.g., a polyurethane foam layer or a neoprene layer) that at least partially surrounds portions of the device 100, which further aids in maintaining heat within the assembly and further minimizes, reduces, and/or eliminates heat dissipation from inside the assembly to outside the assembly while the assembly is in operation/use. In certain aspects, the waterproof outer sheath 300 may be comprised of a woven nylon fabric that is the outermost surface of the sheath (e.g., a shell), and in certain instances, includes a thermally conductive material that lines the inside of sheath that is configured to maintain heat therein (e.g., heat emanating from the radiant heat foot warming device internally within the assembly to reduce, minimize, and/or eliminate heat dissipation externally outside of the assembly). In certain preferred aspects, the waterproof outer sheath 300 is formed of a rip stop woven nylon fabric that at least forms the outermost surface of the sheath, which is a very durable fabric that can withstand extremely harsh environments, and in certain instances, includes a thermally conductive material such as a thermally conductive padding of foam layer 330 (e.g., a polyurethane foam layer) that lines the inside of sheath that is configured to maintain heat therein to reduce, minimize, and/or eliminate heat dissipation externally outside of the assembly.

In view of FIG. 11 and when the assembly 400 is viewed from the top, the waterproof outer sheath 300 includes a first opening 320 (or a plurality of openings in other embodiments such as the two first openings 320 shown in FIG. 11) aligned with the one or more heating zones 120, 121 on the top planar surface 101 of the radiant foot warming device 100 positioned internally within the sheath, with the sheath 300 and device 100 arranged to form an internal compartment (shown in cross-hatch 350 in the cross-sectional views of FIGS. 12A-12C) positioned internally within the assembly 400 between the outer sheath 300 and top planar surface 101 of the radiant foot warming device 100 and further aligned with heating zones 120, 121. The internal compartment 350 is configured to receive and heat a user's feet therein while maintaining a dry environment and/or preventing water intrusion within the internal compartment 350 when the assembly 400 is in use.

In view of FIG. 11 in further view of the cross-sectional views in FIGS. 12A-12C, FIG. 11 further depicts a resiliently deformable elastomeric material/seal(s) 322 that, in certain aspects, is affixed to peripheral edges 321 (inner peripheral edges) of the first opening 320 of the outer sheath 300 and extends inwardly from the peripheral edges 321 of the first opening 320 of the outer sheath towards the center of the first opening. The resiliently deformable elastomeric seal 322 having a slit 323 arranged in and/or proximate to the center of the first opening 320; the resiliently deformable elastomeric material/seal(s) 322 is configured to temporarily open (via the slit 322) while receiving the user's feet therethrough (not shown) and to resiliently close around the user's ankle and/or leg when the user's feet (not shown) are positioned within the internal compartment to maintain a dry environment and/or preventing water intrusion within the internal compartment 350 (shown in cross-hatch in FIGS. 12A-12C) while the assembly 400 is in use/warming the user's feet. The deformable elastomeric material/seal(s) 322 may be comprised of a natural or synthetic rubber, which includes, but is not limited to, a nitrile rubber, a butyl rubber such as butadiene, or an ethylene propylene diene monomer rubber (EPDM rubber) having sufficient rigidity and/or Shore A hardness to open and close as discussed immediately above.

In view of FIG. 11 and in certain aspects, the outer sheath 300 includes a second opening 311 aligned with the adjustable temperature control 111 such that device temperature and temperature controls are viewable, accessible, and controllable by the user when the outer sheath 300 is positioned thereon.

Figure 12A:
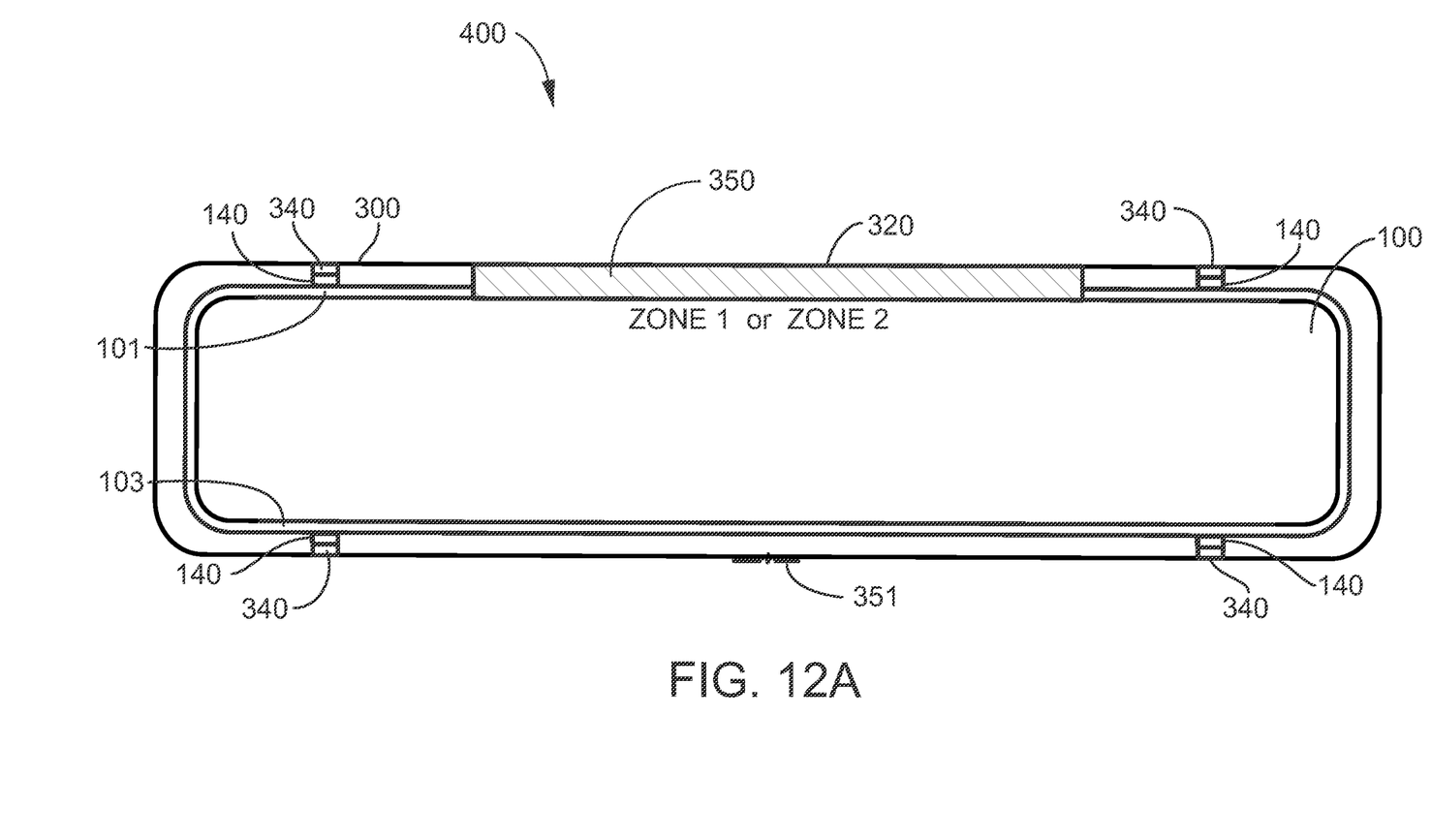
FIG. 12A depicts a cross-section of one embodiment of radiant heat foot warming assembly.
Figure 12B:
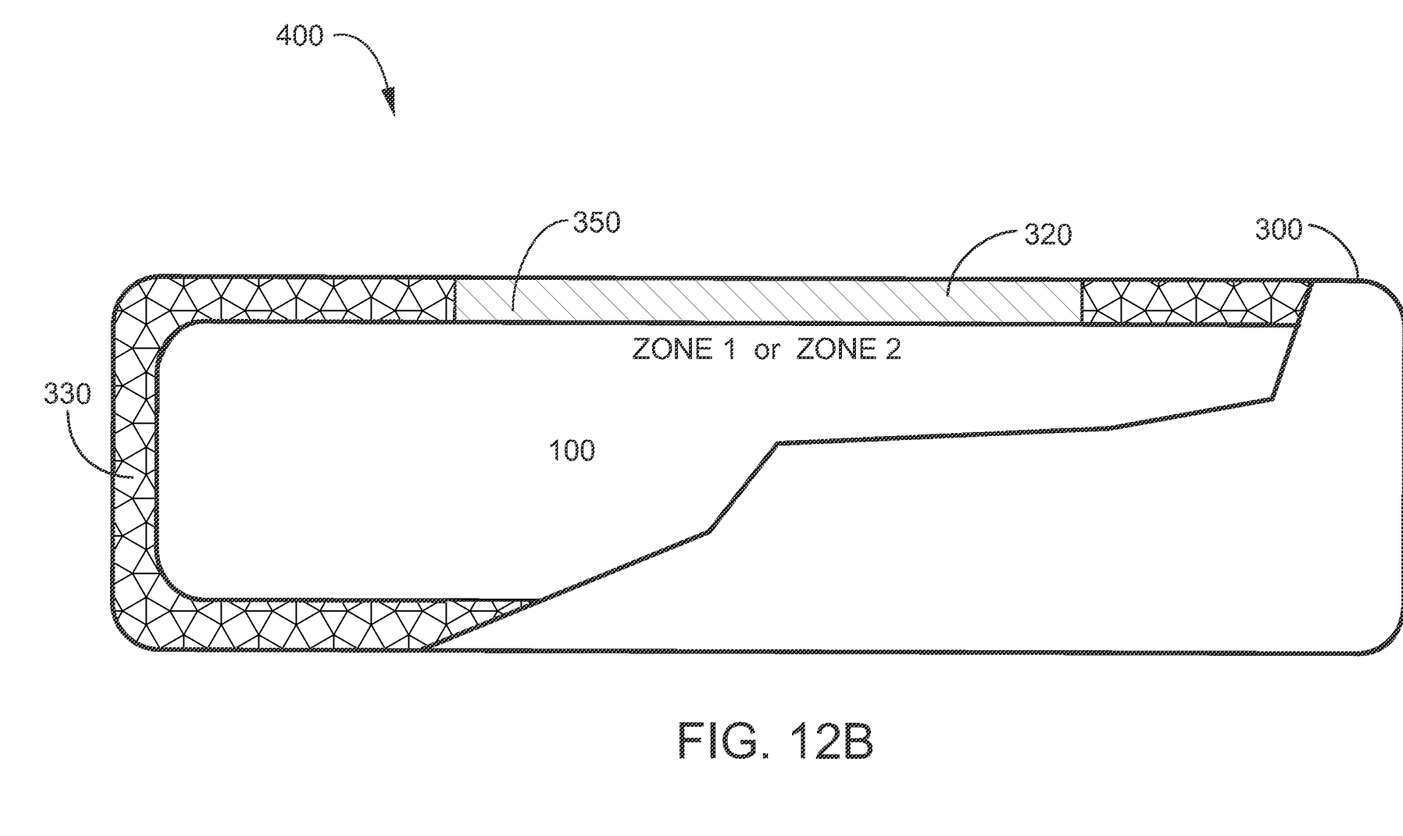
FIG. 12B depicts a cross-section of another embodiment of radiant heat foot warming assembly.
Figure 12C:
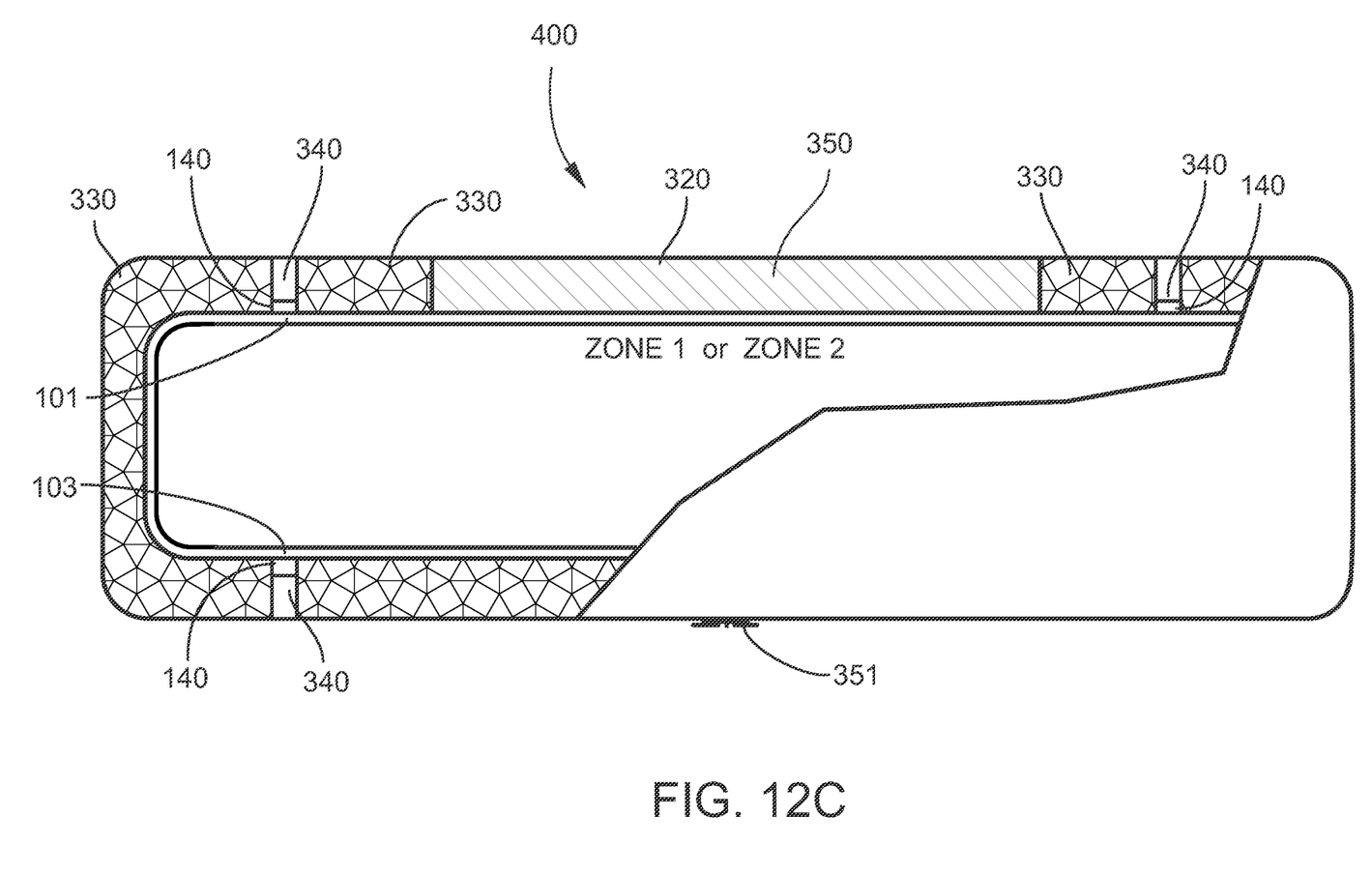
FIG. 12C depicts a cross-section of yet another embodiment of radiant heat foot warming assembly.

FIGS. 12A and 12C depict cross-section views of various embodiments of radiant heat foot warming assembly 400 in which the device 100 is insertable into and/or removable from opening 350 within the bottom side of the outer sheath. Opening 351 may further include a zipper or fastener (e.g., buttons or hook and loop fasteners) affixed to opening 351 that allows for selective opening and closing of opening 350 while positioning device 100 within and/or removing device 100 from the outer sheath 300. In certain aspects and when the device 100 is removable from the outer sheath, additional securing/fastening means may be desired to securely maintain positioning of the device within the outer sheath 300. In this aspect and in view of FIGS. 12A and 12C, the device 100 may further include a plurality of fasteners 140 (e.g., buttons or hook and loop fasteners) affixed to the top planar and/or bottom planar surfaces 101, 103 of the device 100. Likewise, the outer sheath 300 may further include a plurality of fasteners 340 that are configured to align with and engage the corresponding fasteners 140 positioned on the device 100 such that the device 100 may be further secured internally within the outer sheath 300 by fasteners 140 and 340.

As shown, for example, in FIG. 12B, in certain aspects, the device 100 is permanently included within/secured within and/or to the outer sheath 300. In this aspect, FIG. 12B further depicts the outer sheath 300 having a thermally conductive padding or foam layer 330 positioned therein that part surrounds the device. It is also envisioned in certain embodiments that the device 100 may be permanently positioned in outer sheath 300, but unlike FIG. 12B, the thermally conductive padding 330 may be omitted if so desired.

In certain aspects, a kit comprising the outer sheath 300 and device 100 packaged therein is also envisioned.

It should be further noted that the heating devices 100 and assemblies 400 (including the outer sheath 300) are readily portable such that the devices and assemblies disclosed herein may be easily transported to different locations.

The device(s) 100 and assemblies 400 disclosed above create optimal conditions for an athlete's feet by providing radiant heat thereto regardless of environmental conditions (e.g., extremely cold and/or moist/wet environment), thus potentially improving an athlete's performance by mitigating and/or minimizing the deleterious effects on an athlete's performance often associated with extremely cold and/or moist/wet environments during a sporting event/activity.

The foregoing description provides embodiments of the invention by way of example only. It is envisioned that other embodiments may perform similar functions and/or achieve similar results. Any and all such equivalent embodiments and examples are within the scope of the present invention and are intended to be covered by the appended claims.

PARTS LIST

Top planar surface 101 (and 201)
Bottom planar surface 103
Plurality of Sidewalls 105, 106, 107, 108 (and 207)
Charging Port 109
Adjustable Temperature Control Member 111 (and 211)
Heating Zones 120, 121, 220, 221
External Fasteners Positioned On Device 140
Partition 250

Outer Sheath 300
Opening Displaying Temperature Control Member 311
Foot Opening(s) 320 (aligned with heating zones)
Peripheral Edge(s) 321
Resilient, Waterproof Elastomeric Liner 322
Slit 323
Thermally Conductive Padding 330
Internal Fasteners Positioned Within Sheath 340
Internal Compartment 350
Opening 351 For Removably Positioning Device 100 Within Sheath

What is claimed is:

1. A radiant heat foot warming assembly comprising:
(a) a waterproof outer sheath configured to maintain dryness and/or prevent water intrusion internally within the waterproof outer sheath; and
(b) a radiant foot warming device that is positioned internally within the waterproof outer sheath, the radiant foot warming device including:
(i) a top planar surface configured to emanate radiant heat from one or more heating zones to warm feet of a user;
(ii) a bottom planar surface spaced apart from the top planar surface, the bottom planar surface is configured to not emanate heat therefrom;
(iii) a plurality of curved sidewalls positioned between and connected to the top planar surface and the bottom planar surface, the plurality of sidewalls do not emanate heat therefrom; and
(iv) an adjustable temperature control member positioned on the top planar surface that displays device temperature and further adjustably controls device temperature to regulate radiant heat emanating from the top planar surface, wherein:
the waterproof outer sheath comprises a thermally conductive material configured to maintain heat emanating from the radiant heat foot warming device internally within the assembly to reduce, minimize, and/or eliminate heat dissipation externally outside of the assembly, and the waterproof outer sheath comprises a first opening aligned with the one or more heating zones on the top planar surface of the radiant foot warming device and arranged to form an internal compartment positioned internally within the assembly between the outer sheath and top planar surface of the radiant foot warming device that is configured to receive and heat a user's feet therein while maintaining a dry environment and/or preventing water intrusion within the internal compartment.

2. The radiant heat foot warming assembly of claim 1, further comprising a resiliently deformable elastomeric seal circumferentially affixed to peripheral edges of a first opening of the outer sheath and extending inwardly from the peripheral edges of the first opening of the outer sheath towards a center of the first opening, the resiliently deformable elastomeric seal having a slit arranged in the center of the first opening that is configured to temporarily open while receiving the user's feet therethrough and to resiliently close around the user's ankle and/or leg when the user's feet are positioned within an internal compartment to maintain the dry environment and/or preventing water intrusion within the internal compartment.

3. The radiant heat foot warming assembly of claim 2, the outer sheath comprising a second opening aligned with the adjustable temperature control member such that that the device temperature and temperature control are viewable and accessible by the user.

4. The radiant heat foot warming assembly of claim 3, wherein outer sheath comprises a waterproof nylon material.

5. The radiant heat foot warming assembly of claim 4, wherein the waterproof nylon material is rip stop nylon.

6. The radiant heat foot warming assembly of claim 4, wherein the radiant foot warming device is removable from the waterproof outer sheath.

7. The radiant heat foot warming assembly of claim 4, wherein the radiant foot warming device is permanently positioned within the outer sheath.

* * * * *